(12) United States Patent
Lee et al.

(10) Patent No.: US 6,727,272 B1
(45) Date of Patent: Apr. 27, 2004

(54) LEFLUNOMIDE ANALOGS FOR TREATING RHEUMATOID ARTHRITIS

(75) Inventors: An-Rong Lee, Taipei (TW); Wen-Hsin Huang, Taipei (TW); Jiajiu Shaw, Ann Arbor, MI (US)

(73) Assignee: Unitech Pharmaceuticals, Inc., Ann Arbor, MI (US)

( * ) Notice: Subject to any disclaimer, the term of this patent is extended or adjusted under 35 U.S.C. 154(b) by 136 days.

(21) Appl. No.: 10/195,824

(22) Filed: Jul. 15, 2002

(51) Int. Cl.[7] .................... A61K 31/422; C07D 261/06
(52) U.S. Cl. .......................... 514/378; 548/248
(58) Field of Search ..................... 548/248; 514/378

(56) References Cited

U.S. PATENT DOCUMENTS 5,814,646 A * 9/1998 Heinz et al. ............... 514/363
5,977,151 A 11/1999 Mullner et al.
6,121,479 A 9/2000 Mullner et al.
6,265,588 B1 7/2001 Mullner et al.

OTHER PUBLICATIONS

Goel et al (1997): STN International, CAPLUS database, (Columbus, Ohio), No. 127:28623. Structural Chemistry, vol. 8(2), 155–159.*

* cited by examiner

Primary Examiner—Joseph K. McKane
Assistant Examiner—Golam M. M. Shameem
(74) Attorney, Agent, or Firm—Brinks Hofer Gilson & Lione; Gregory H. Zayia

(57) ABSTRACT

Novel leflunomide analogs were synthesized and evaluated in-vivo. Based on the in-vivo studies, these analogs are surprisingly effective for treating rheumatoid arthritis.

28 Claims, 2 Drawing Sheets

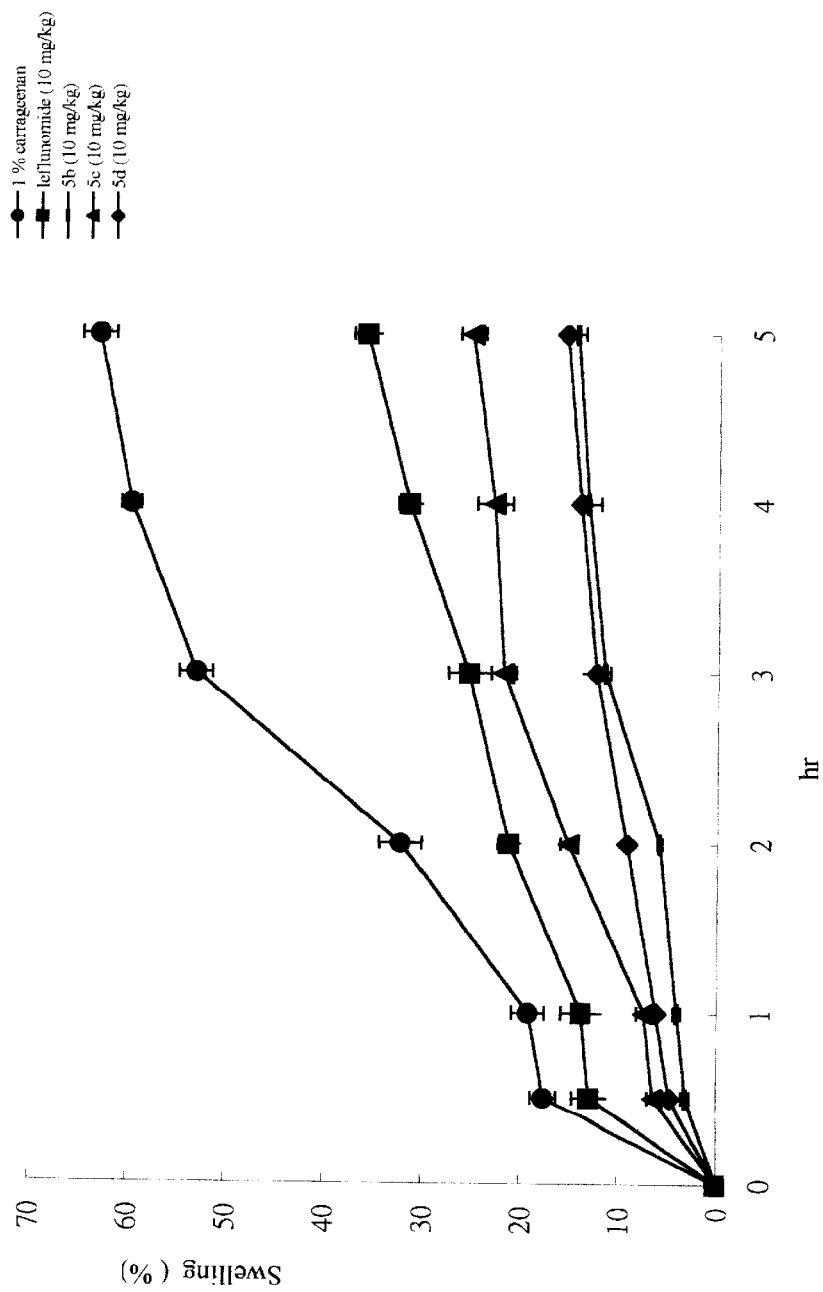
Fig. 1 The edema percentage of carrageenan-induced left paw edema after treatment with drugs. Each value represents the mean ±S.D. of 5 animals.

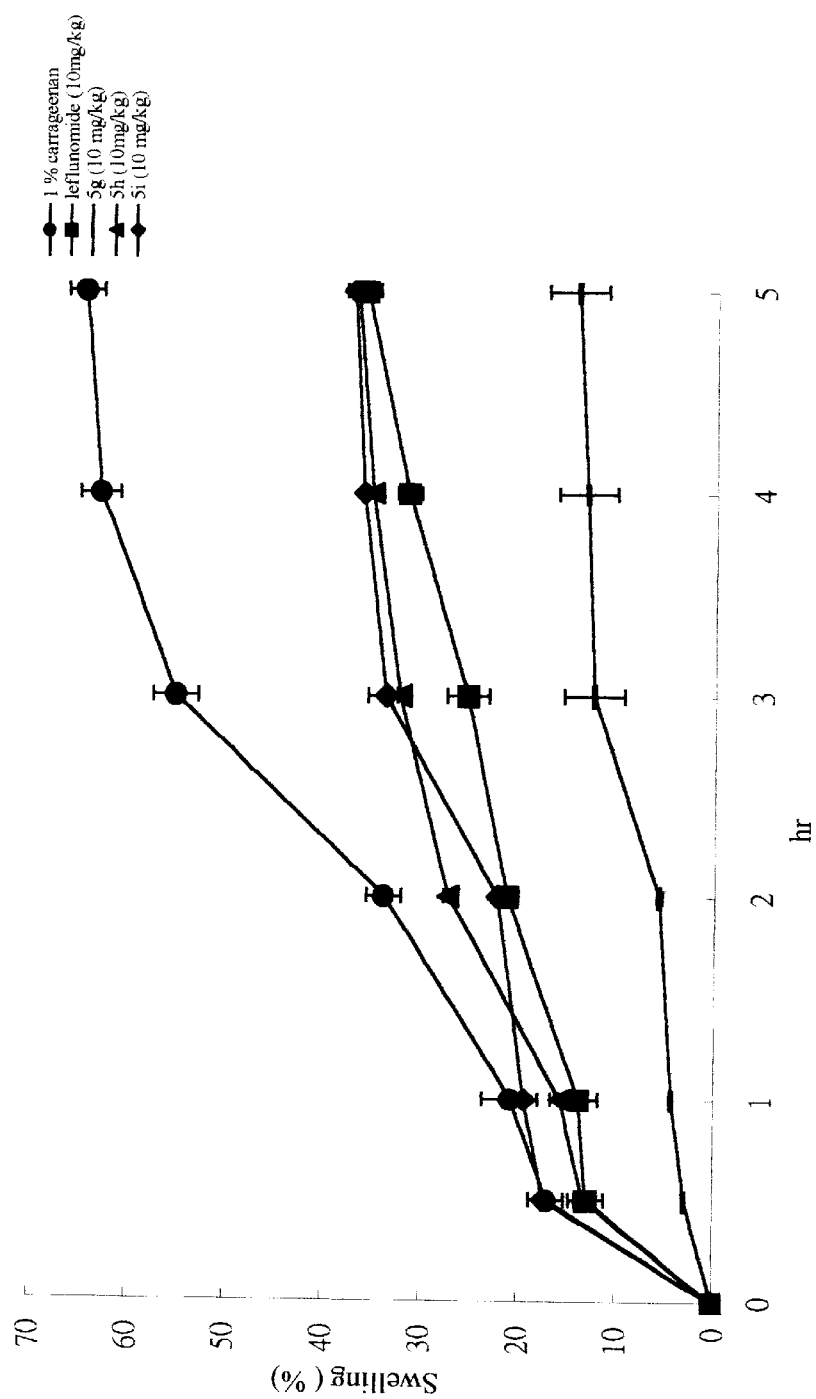
Fig. 2 The edema percentage of carrageenan-induced left paw edema after treatment with drugs. Each value represents the mean ±S.D. of 5 animals.

LEFLUNOMIDE ANALOGS FOR TREATING RHEUMATOID ARTHRITIS

BACKGROUND

Rheumatoid arthritis (hereinafter referred to as RA) is a chronic disease that inflames joints and nearby areas. Besides the joints, other tissues can also be affected by RA. Patients with RA usually have overreactive T cells. Therefore, RA can be categorized as an autoimmune disease.

Leflunomide, N-(4-trifluoromethylphenyl)-4-carboxamidyl-5-methylisoxazole, is a drug for treating RA introduced into the market in recent years. Leflunomide and its main metabolite, malononitrilamide (MNA), were first made by Hoechst Marion Roussel.

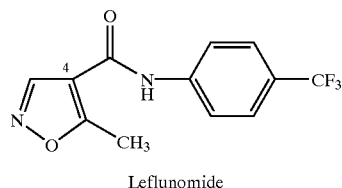

Leflunomide

OBJECTIVES

The objectives of this invention are as follows:
1. To synthesize a series of novel analogs of leflunomide,
2. To conduct in-vivo studies to evaluate the efficacy of the analogs, and
3. To select the leflunomide analogs that can be used for treating rheumatoid arthritis.

DETAILED DESCRIPTION OF THE INVENTION

This invention comprises the syntheses of a series of novel analogs of leflunomide for treating Rheumatoid Arthritis. To the best of our knowledge, these analogs have not been disclosed by any other parties. The in-vivo animal studies indicate that these leflunomide analogs are surpassingly more effective than leflunomide.

Representative syntheses and in-vivo animal studies are described as follows:

A. Methods of Syntheses

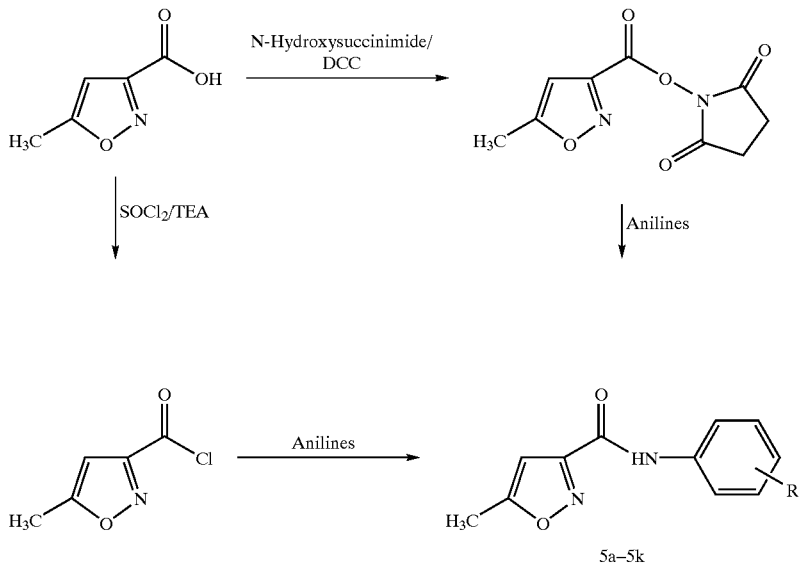

Wherein DCC is N,N'-dicyclohexylcarbodiimide and TEA is triethylamine.

| Analog | 5a | 5b | 5c | 5d | 5e | 5f | 6g | 5h | 5i | 5j | 5k |
|---|---|---|---|---|---|---|---|---|---|---|---|
| R | 4-H | 2-Cl | 3-Cl | 4-Cl | 3-$CF_3$ | 4-$CF_3$ | 2,4-$(Cl)_2$ | 4-$OCH_3$ | 3,4,5-$(OCH_3)_3$ | 4-COOH | 4-F |

Method 1:

Weigh 1 g of 5-methylisoxazole-3-carboxylic acid; dissolve it in 10 mL of chloroform in a reactor. Place the reactor in an ice bath and add 1.2 mL of thionyl chloride. Gradually add 1 mL of triethylamine. Reduce the volume under vacuum after the reaction is complete. Add dichloromethane (10 mL) and then add the desired substituted aniline (see the table above) and mix thoroughly with cooling from an ice bath. Add triethylamine (1 mL), let it react for about 30 minutes, and monitor the reaction by thin layer chromatography. Wait till the reaction is complete and concentrate under vacuum. Use a separatory funnel to separate the organic and aqueous layers. Keep the organic layer; add anhydrous magnesium sulfate; let it sit for about 30 minutes; filter off magnesium sulfate and keep the filtered organic liquid; dry the organic liquid to obtain the crude product; re-crystallize in absolute alcohol to obtain product 5a and 5b.

| Product | Aniline mL | Yield g (%) | Appearance |
|---|---|---|---|
| 5a | 1.1 | 0.1 (4.2) | Yellow crystals |
| 5b | 1 | 0.1 (7.2) | Off-white crystals |

Method 2:

Weigh 5-methylisoxazole-3-carboxylic acid (2 g), N-hydroxysuccinimide (2 g) and coupling agent N,N'-dicyclohexylcarbodiimide (3.6 g); add the desired substituted aniline, and crystallize in absolute alcohol to make 5a~5k.

| Product | Anilines mL | Yield g (%) | Appearance |
|---|---|---|---|
| 5a | 2 mL | 1.0 (71) | Yellow crystals |
| 5b | 2 mL | 0.9 (20.2) | Off-white crystals |
| 5c | 2 mL | 2.4 (53.8) | White crystals |
| 5d | 2.4 g | 8.7 (45) | White crystals |
| 5e | 2 mL | 3.8 (89.1) | White crystals |
| 5f | 2 mL | 1.6 (37) | White crystals |
| 5g | 3.4 g | 4.2 (73.2) | Off-white crystals |
| 5h | 2.1 g | 0.76 (18.9) | Gray crystals |
| 5i | 3.2 g | 2 (39.6) | Gray crystals |
| 5j | 2.4 g | 1.9 (44.6) | Light-brown crystals |
| 5k | 2 mL | 0.9 (21.6) | White crystals |

B. Results of Syntheses

Results of the syntheses and characteristics of the leflunomide analogs are shown as follows:

[Compound 5a] N-(Phenyl)-3-carboxamidyl-5-methylisoxazole

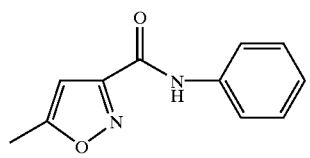

mp: 109~110° C.; UV (MeOH): $\lambda_{max}$nm (log ε)=270 (4.025); IR (KBr): vcm$^{-1}$=3339 (N—H), 1677(C=O), 1598 (C=C); MS (EI, 70ev): 202 (M$^+$, 100), 119 (65); $^1$H-NMR (DMSO-d$_6$, –300 MHz): δ(ppm); 2.47 (3H, s, CH$_3$), 6.65 (1H, s, CCH), 7.11 (1H, t, J=6.6 Hz, H$_4$-phenyl), 7.34 (2H, t, J=7.5 Hz, H$_{3,5}$-phenyl), 7.80 (2H, d, J=9 Hz, H$_{2,6}$-phenyl), 10.64 (1H, s, NH); $^{13}$C-NMR (DMSO-d$_6$, 75 MHz): δ(ppm); 12.1, 101.9, 120.9, 124.6, 129.0, 138.4, 157.8, 159.6, 171.7; CHN Analysis (Theory/Experiment) based on C$_{11}$H$_{10}$N$_2$O$_2$; % C; (65.34/65.28), % H; (4.98/4.95), % N; (13.85/13.72).

[Compound 5b] N-(2-Chlorophenyl)-3-carboxamidyl-5-methylisoxazole)

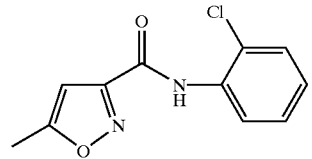

mp: 90~92° C.; UV (MeOH): $\lambda_{max}$nm (log ε)=250 (3.33); IR (KBr): vcm$^{-1}$=3326 (N—H), 1626 (C=O), 1575 (C=C); MS (EI, 70ev): 236 (M$^+$), 201 (100), 173 (60); $^1$H-NMR (DMSO-d$_6$, –300 MHz): δ(ppm); 2.50 (3H, s, CH$_3$), 6.69 (1H, s, CCH), 7.29 (1H, t, J=7.7 Hz, H$_4$-phenyl), 7.39 (1H, t, J=7.7 Hz, H$_5$-phenyl), 7.55 (1H, d, J=7.8 Hz, H$_3$-phenyl), 7.71 (1H, d, J=7.9 Hz, H$_6$-phenyl), 10.19 (1H, s, NH); $^{13}$C-NMR (DMSO-d$_6$, 75 MHz): δ(ppm); 12.24, 101.8, 127.1, 128.0, 129.9, 134.2, 157.7, 158.9, 172.2; CHN Analysis (Theory/Experiment) based on C$_{11}$H$_9$ClN$_2$O$_2$. % C; (55.83/55.36), % H; (3.83/3.77), % N; (11.84/11.99).

[Compound 5c] N-(3-Chlorophenyl)-3-carboxamidyl-5-methylisoxazole

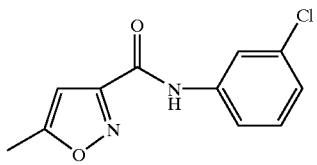

mp: 91~93° C.; UV (MeOH): $\lambda_{max}$nm (log ε)=260 (4.01); IR (KBr): vcm$^{-1}$=3347 (N—H), 1689 (C=O), 1593 (C=C); MS (EI, 70ev): 236 (M$^+$), 173 (100), 153 (80); $^1$H-NMR (DMSO-d$_6$, –300 MHz): δ(ppm); 2.49 (3H, s, CH$_3$), 6.66 (1H, s, CCH), 7.18 (1H, d, J=8 Hz, H$_4$-phenyl), 7.37 (1H, t, J=8.1 Hz, H$_5$-phenyl), 7.72 (1H, d, J=8.3 Hz, H$_6$-phenyl), 7.94 (1H, s, H$_2$-phenyl), 10.82 (1H, s, NH); $^{13}$C-NMR (DMSO-$_6$, 75 MHz): δ(ppm); 12.2, 120.0, 119.2, 120.3, 124.3, 130.7,133.3, 139.9,.158.0, 159.3, 171.9; CHN Analysis (Theory/Experiment) based on C$_{11}$H$_9$ClN$_2$O$_2$; % C; (55.83/55.93), % H; (3.83/3.75), % N; (11.84/11.84).

[Compound 5d] N-(4-Chlorophenyl)-3carboxamidyl-5-methyisoxazole

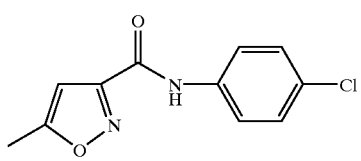

mp: 135~140° C.; UV (MeOH): $\lambda_{max}$nm (log ε)=234 (4.55), 269 (4.74); IR (KBr): vcm$^{-1}$=3329 (N—H), 1683 (C=O), 1528 (C=C); MS (EI, 70ev): 236 (100), 201(M$^+$); $^1$H-NMR (DMSO-d$_6$, –300 MHz): δ(ppm); 2.50 (3H, S, CH$_3$), 6.68 (1H, s, CCH), 7.71 (2H, d, J=8.1 Hz, H$_{3,5}$-phenyl), 8.02 (2H, d, J=7.8 Hz, H$_{2,6}$-phenyl), 10.98 (1H, s, NH); $^{13}$C-NMR (DMSO-$_6$, 75 MHz): δ(ppm); 12.1, 101.9, 122.4, 128.4, 128.9, 137.4, 157.9, 159.4, 171.7; CHN Analysis (Theory/Experiment) based on C$_{11}$H$_9$ClN$_2$O$_2$; % C; (55.83/55.93), % H; (3.83/3.98), % N; (11.84/11.17)

[Compound 5e] N-(3-Trifluoromethyl)-3-carboxamidyl-5-methylisoxazole

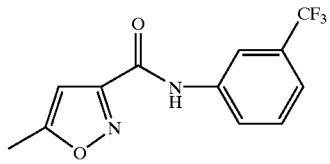

mp: 156~158° C.; UV (MeOH): $\lambda_{max}$nm (log $\epsilon$)=255 (4.098); IR (KBr): 3330 (N—H), 1683 (C=O), 1557 (C=C); MS (EI, 70ev): 271 (M$^+$, 90), 102 (100); $^1$H-NMR (DMSO-d$_6$, –300 MHz): $\delta$(ppm); 2.49 (3H, s, CH$_3$), 6.68 (1H, s, CCH), 7.47 (1H, d, J=7.3 Hz, H$_4$-phenyl), 7.57 (1H, t, J=7.9 Hz, H$_5$-phenyl), 8.04 (1H, d, J=8.1 Hz, H$_6$-phenyl), 8.26 (1H, s, H$_2$-phenyl), 10.99 (1H, s,NH); $^{13}$C-NMR (DMSO-d$_6$, 75 MHz): $\delta$(ppm); 12.2, 101.9, 117.0, 117.1, 120.9, 124.5, 130.1, 130.3, 139.3, 158.2, 159.3, 171.9; CHN Analysis (Theory/Experiment) based on C$_{12}$H$_9$F$_3$N$_2$O$_2$; % C; (53.34/53.39), % H; (3.36/3.59), % N; (10.37/10.71).

[Compound 5f] N-(4-Trifluoromethylphenyl)3-carboxamidyl-5-methylisoxazole

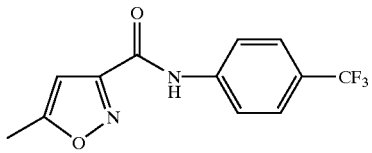

mp 179~180° C.; UV (MeOH): $\lambda_{max}$nm (log $\epsilon$)=268 (3.887); IR (KBr): vcm$^{-1}$=3334 (N—H), 1677(C=O), 1539 (C=C); MS (EI, 70ev): 270 (M$^+$, 100); $^1$H-NMR (DMSO-d$_6$, –300 MHz): $\delta$(ppm): 2.49 (3H, s, CH$_3$), 6.68 (1H, s, CCH), 7.71 (2H, d, J=8 Hz, H$_{2,6}$-phenyl), 8.03 (2H, d, J=8.2 Hz, H$_{3,5}$-phenyl), 10.99 (1H, s, NH); $^{13}$C-NMR (DMSO-d$_6$, 75 MHz): $\delta$(ppm); 12.1, 101.9, 122.4, 128.4, 128.9, 137.4, 157.8, 159.4, 171.7; CHN Analysis (Theory/Experiment) based on C$_{12}$H$_9$F$_3$N$_2$O$_2$; % C; (53.34/53.01), % H; (3.36/3.46), % N; (10.37/10.38).

[Compound 5g] N-(2,4-Dichlorophenyl)-3carboxamidyl-5-methylisoxazole

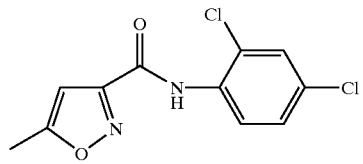

mp: 148~156° C.; UV (MeOH): $\lambda_{max}$nm (log $\epsilon$)=250 (4.89), 277 (3.88); IR (KBr): vcm$^{-1}$=3348 (N—H), 1697 (C=O), 1589 (C=C) MS (EI, 70ev): 271 (100), 154(M$^+$); $^1$H-NMR (DMSO-d$_6$, –300 MHz): $\delta$(ppm): 2.50 (3H, s, CH$_3$), 6.67 (1H, s, CCH), 7.41 (1H, d, J=8.7 Hz H$_5$-phenyl), 7.66 (1H, d, J=2.2 Hz, H$_3$-phenyl, 7.83 (1H, d, J=8.7 Hz, H$_6$-phenyl), 10.25 (1H, s, NH); CHN Analysis (Theory/Experiment) based on C$_{11}$H$_8$Cl$_2$N$_2$O$_2$; % C; (48.73/48.14), % H; (2.97/2.97), % N; (10.33/10.35).

[Compound 5h] N-(4-Methoxyphenyl)-3carboxamidyl-5-methylisoxazole

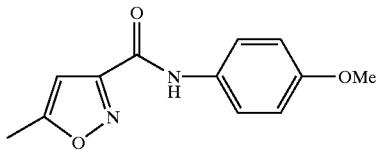

mp: 124~126° C.; UV (MeOH): $\lambda_{max}$nm (log $\epsilon$)=227 (3.76), 288 (3.69); IR (KBr): vcm$^{-1}$=3332 (N—H), 1672 (C=O), 1521 (C=C); MS (EI, 70ev): 232 (M$^+$, 100), 149 (64); $^1$H-NMR (DMSO-d$_6$, –300 MHz): $\delta$(ppm); 2.48 (3H, s, CH$_3$), 3.73 (3H, s, OCH$_3$), 6.63 (1H, s, CH$_3$), 6.91 (2H, d, J=8 Hz, H$_{3,5}$-phenyl), 7.69 (2H, d, J=8.1 Hz, H$_{2,6}$-phenyl), 10.52 (1H, s, NH); $^{13}$C-NMR (DMSO-d$_6$, 75 MHz): $\delta$(ppm); 10 12.2, 55.5, 101.9, 114.1, 122.3, 122.4, 131.5, 156.3, 157.4, 159.7, 171.6; CHN Analysis (Theory/Experiment) based on C$_{11}$H$_{12}$N$_2$O$_3$; % C; (62.06/62.12), % H; (5.21/5.23), % N; (12.06/12.33);

[Compound 5i] N-(3,4,5-Trimethoxyphenyl)-3-carboxamidyl-5-methylisoxazole

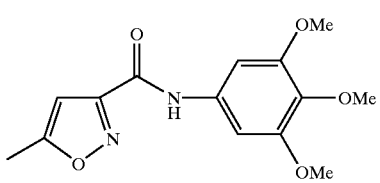

mp: 170~172° C.; UV (MeOH): $\lambda_{max}$nm (log $\epsilon$)=293 (3.439); IR (KBr): vcm$^{-1}$=3326 (N—H), 1688 (C=O), 1557 (C=C); MS (EI, 70ev): 292 (M$^+$, 100), 277 (20); $^1$H-NMR (DMSO-d$_6$, –300 MHz): $\delta$(ppm): 2.49 (3H, s, CH$_3$), 3.63 (6H, s, 2OCH$_3$), 3.75 (3H, s, OCH$_3$), 6.35 (1H, s, CCH$_3$), 7.25 (2H, s, H$_{2,6}$-phenyl), 10.52 (1H, s, NH); CHN Analysis (Theory/Experiment) based on C$_{11}$H$_{12}$N$_2$O$_3$; % C; (57.53/57.65), % H; (5.52/5.61), % N; (9.58/9.59).

[Compound 5j] 4-[(5-Methylisoxazole-3-carbonyl)-amino]-benzoic acid

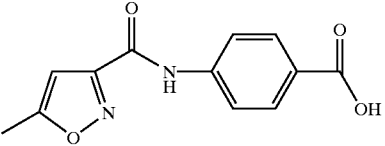

mp: 267~270° C.; UV (MeOH ): m$\lambda_{max}$nm (log $\epsilon$)=284 (4.27); IR (KBr): vcm$^{-1}$=3342 (N—H), 1685 (C=O), 1529 (C=C); MS (FAB): m/z 247 (MH$^+$); $^1$H-NMR (DMSO-d$_6$, –300 MHz): $\delta$(ppm): 2.50 (3H, s, CH$_3$), 6.69 (1H, s, CCH), 7.94 (4H, s, H$_{2,3,5,6}$-phenyl), 10.94 (1H, s, NH); $^{13}$C-NMR (DMSO-d$_6$, 75 MHz): $\delta$(ppm); 12.2, 102.1, 120.2, 126.6, 130.6, 142.5, 158.2, 159.4, 167.2, 171.9; CHN Analysis (Theory/Experiment) based on C$_{11}$H$_9$ClN$_2$O$_2$; % C; (58.54/58.46), % H; (4.09/4.10), % N; (11.38/11.42).

[Compound 5k] N-(4-Fluorophenyl)-3-carboxamidyl-5-methylisoxazole

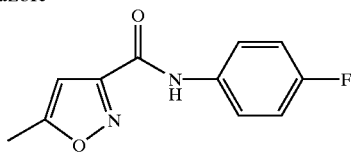

mp: 136~138° C.; UV (MeOH): $\lambda_{max}$nm (log $\epsilon$)=271 (4.19); IR (KBr): $vcm^{-1}$=3342 (N—H), 1685 (C=O), 1529 (C=C); MS (EI, 70ev): 220 ($M^+$, 100), 137 (30), 110 (38); $^1$H-NMR (DMSO-$d_6$, −300 MHz): δ(ppm); 2.49 (3H, s, $CH_3$), 6.65 (1H, s, CCH), 7.10 (2H, dd, J=5.2, 5.1 Hz, $H_{2,6}$-phenyl), 7.80 (2H, dd, J=8.8, 8.6 Hz, $H_{3,5}$-phenyl), 10.71 (1H, s, NH); $^{13}$C-NMR (DMSO-$d_6$, 75 MHz): δ(ppm); 12.2, 101.9, 115.5, 122.7, 134.7, 157.7, 159.5, 160.6, 171.7; CHN Analysis (Theory/Experiment) based on $C_{12}H_9FN_2O_2$; % C; (60.0/60.17), % H; (4.12/4.17), % N; (12.72/12.47).

C. In-Vivo Experiments

C-1. Animal Used

Wistar Albino Rats of 4 to 6 weeks old with weights of 100–150 g were used for the studies.

C-2. Preparation of reagents 1.1 % carrageenan solution

Weigh 30 mg of λ-carrageenan (Sigma Chemical) powder; add 3 mL of saline to make the 1% carrageenan solution.

2. CMC (carboxymethyl cellulose) solution

Weigh 30 mg of λ-carrageenan (Sigma Chemical) powder; add 3 mL of saline to make the 1% carrageenan solution.

3. Dexamethasone suspension

Weigh 7.5 mg of dexamethone (Sigma Chemical Co., USA), add 5 mL of 1% CMC solution, shake to make the 1.5 mg/mL dexamethasone suspension.

4. Ibuprofen suspension Weigh 10 mg of ibuprofen (Sigma Chemical Co., USA), add 10 mL of 1% CMC solution, shake to make the 1 mg/ml ibuprofen suspension.

5. Suspensions of testing compounds

Individually weigh 10 mg of each testing compound; add 10 mL of 1% CMC and shake to make the suspension.

6. Solution used to measure the inflammation

Weigh 0.4–0.5 g of NaCl; add 5 mL of surfactant, Lubricant IMBIBNTE BBC97 (Chimifoto ornano S. P. A. Italy); Add de-ionized water to make 1 liter.

C-3. Efficacy and Results

In the present invention, Carrageenan was used to stimulate the inflammation on the rear left footpad of the rat. The inflammation on the left footpad of each rat was measured for rats with and without treatment. Treatment includes leflunomide analogs, dexamethasone, ibuprofen, and Malononitrilamide (MNA). Measurements of the inflamation at pre-determined time points were made.

The rats were weighed and divided into three groups: (1) Control Group, (2) Test Group, and (3) Comparison Group. For each compound, 5 rats were used and marked on the tails. Before injecting carrageenan, the volume of each left footpad was measured ($V_0$). Each rat was injected in the back as follows:

(1) Control Group: 1% CMC for Control Group, (2) Testing Group: testing compound (10 mg/kg each) in 1% CMC, and (3) Comparison Group: dexamethasone (1.5 mg/kg in 1% CMC), ibuprofen 10 mg/kg in 1% CMC, MNA in 1% CMC.

One hour later, 0.05 mL of 1% carrageenan was injected onto the rear footpad of each rat to initiate the inflammation. Measure the volume of the rear left footpad ($V_t$) at 0.5, 1, 2, 3, 4, and 5 hours.

The Edema Rate (E%) and the Inhibition Rate (I%) are calculated as follows and the results of the in-vivo studies are summarized in Table 1 and Table 2.

$$E\% = \frac{V_t - V_0}{V_0} \times 100\%$$

$$I\% = \frac{E_c - E_t}{E_c} \times 100\%$$

$V_0$=Volume (mL) of the rear left footpad before the injection of Carrageenan.

$V_t$=Volume (mL) of the rear left footpad at "t" time after the injection of Carrageenan $E_c$=Edema Rate of the, Control Group $E_t$=Edema Rate of the Testing Group and Comparison Group

TABLE 1

Efficacy of Dexamethasone, ibuprofen, leflunomide, and malononitrilamide

| Groups | Dose (mg/kg) | Edema rate[a] (E%) after carrageenan administration | | | | |
|---|---|---|---|---|---|---|
| | | 1 hr | 2 hr | 3 hr | 4 hr | 5 hr |
| Control | | 20.8 ± 2.9 | 33.8 ± 1.8 | 55.3 ± 2.4 | 63 ± 2.1 | 64.5 ± 1.8 |
| Dexamethasone | 1.5 | 5.5 ± 0.7 (73.6)[b] | 12 ± 1.8 (64.5) | 18.9 ± 1.5 (65.8) | 21.1 ± 0.4 (66.5) | 21.7 ± 0.4 (66.4) |
| Ibuprofen | 10 | 18.9 ± 1.1 (9.1) | 26.5 ± 1.4 (21.6) | 29.9 ± 0.1 (45.9) | 35 ± 0.9 (44.4) | 40 ± 0.41 (38) |
| | 20 | 11.5 ± 1.8 (20.8) | 19.2 ± 0.4 (43.2) | 24.5 ± 1.1 (55.7) | 28.3 ± 1.5 (55.1) | 31.2 ± 1.6 (51.6) |
| | 30 | 6.2 ± 0.2 (65.4) | 10.9 ± 0.6 (67.8) | 11.2 ± 0.2 (79.7) | 15.8 ± 0.7 (74.9) | 30.3 ± 4.2 (53) |
| Leflunomide | 5 | 20 ± 0.9 (3.8) | 27.2 ± 0.5 (19.5) | 32.6 ± 0.7 (41) | 38.7 ± 0.5 (38.6) | 39.8 ± 1.2 (38.3) |
| | 10 | 14.9 ± 1.2 (28.4) | 22.2 ± 1.2 (34.3) | 24.9 ± 2.4 (55) | 32.9 ± 1.3 (47.8) | 34.8 ± 1.4 (46) |
| | 20 | 11.3 ± 0.8 (45.7) | 16.9 ± 1.1 (50) | 21.9 ± 1.2 (60.4) | 25 ± 1.5 (60.3) | 27.5 ± 0.9 (57.4) |
| Malononitrilamide (MNA) | 10 | 15.2 ± 1.5 (26.9) | 17.6 ± 1 (47.9) | 20.5 ± 0.5 (63) | 21.7 ± 0.9 (65.6) | 24.2 ± 1.3 (62.5) |

[a]Each value represents the mean ± S.D. of 5 animals.
[b]The number in parentheses indicates the percentage inhibition rate (I %).

TABLE 2

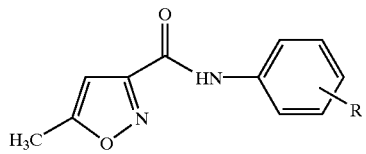

Efficacy of N-(Substituted-phenyl)-3-carboxamidyl-5-methylisoxazoles

| Groups | R | Dose (mg/kg) | Edema rate[a] (E%) after carrageenan administration | | | | |
|---|---|---|---|---|---|---|---|
| | | | 1 hr | 2 hr | 3 hr | 4 hr | 5 hr |
| Control | | | 20.8 ± 2.9 | 33.8 ± 1.8 | 55.3 ± 2.4 | 63 ± 2.1 | 64.5 ± 1.8 |
| Leflunomide | | 10 | 14.9 ± 1.2 (28.4)[b] | 22.2 ± 1.2 (34.3) | 24.9 ± 2.4 (55) | 32.9 ± 1.3 (47.8) | 34.8 ± 1.4 (46) |
| 5a | 4-H | 10 | 7.8 ± 1.2 (62.5) | 8.5 ± 0.3 (74.9) | 11.7 ± 0.5 (78.8) | 13.6 ± 0.8 (78.4) | 35.8 ± 1.4 (44.5) |
| 5b | 2-Cl | 10 | 4.1 ± 0.4 (80.1) | 5.9 ± 0.4 (82.5) | 11.4 ± 0.5 (79.4) | 13.2 ± 1.2 (79) | 14.4 ± 0.8 (77.7) |
| 5c | 3-Cl | 10 | 7.4 ± 0.7 (64.4) | 15.1 ± 0.8 (55.3) | 21.8 ± 1.3 (60.6) | 22.8 ± 1.8 (63.8) | 25.1 ± 1.3 (61.1) |
| 5d | 4-Cl | 10 | 6.2 ± 0.7 (70.2) | 9.2 ± 0.3 (72.8) | 12.4 ± 1.4 (77.6) | 14 ± 1.1 (77.8) | 15.5 ± 0.6 (76) |
| 5e | 3-CF$_3$ | 10 | 15.4 ± 0.3 (26) | 19.7 ± 1.7 (41.7) | 32.8 ± 2.7 (40.7) | 35.3 ± 0.9 (44) | 34.3 ± 3.2 (46.8) |
| 5f | 4-CF$_3$ | 10 | 11.2 ± 0.9 (46.2) | 15.6 ± 0.4 (53.8) | 25.1 ± 0.2 (54.6) | 26.2 ± 0.1 (58.4) | 26.9 ± 0.5 (58.3) |
| 5g | 2,4-(Cl)$_2$ | 10 | 4.3 ± 0.1 (79.3) | 5.7 ± 0.3 (83.1) | 12.5 ± 3.1 (77.4) | 13.2 ± 3 (79) | 14.2 ± 3 (78) |
| 5h | 4-OCH$_3$ | 10 | 15.8 ± 0.9 (24) | 27.4 ± 0.4 (18.9) | 32.3 ± 0.3 (41.6) | 35.1 ± 0.8 (44.3) | 36.7 ± 0.4 (43.1) |
| 5i | 3,4,5-(OCH$_3$)$_3$ | 10 | 19.4 ± 0.4 (6.7) | 22.3 ± 0.1 (34) | 33.7 ± 1.9 (39.1) | 36.1 ± 0.1 (42.7) | 37.1 ± 0.8 (42.5) |
| 5j | 4-COOH | 10 | 10.3 ± 0.6 (50.5) | 18 ± 1 (46.7) | 24.2 ± 2.3 (56.2) | 26.3 ± 0.7 (58.3) | 27.5 ± 0.9 (57.4) |
| 5k | 4-F | 10 | 11.2 ± 1.5 (46.2) | 27.9 ± 2.5 (17.5) | 33.9 ± 1.8 (38.7) | 35.6 ± 0.6 (43.5) | 36.3 ± 0.02 (43.7) |

[a]Each value represents the mean ± S.D. of 5 animals.
[b]The number in parentheses indicates the percentage inhibition rate (I%).

In the present invention, a compound with the following general formula (I) is disclosed,

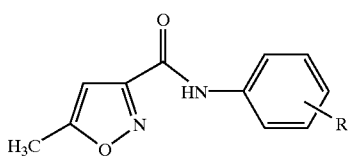

(I)

wherein R is —H, 2-Cl, 3-Cl, 4-Cl, 2,4-(Cl)$_2$, 2-F, 3-F, 4-F, 2,4-(F)$_2$, 2-Br, 3-Br, 4-Br, 2,4-(Br)$_2$, 2-CF$_3$, 3-CF$_3$, 4-CF$_3$, 2,4-(CF$_3$)$_2$, 2-COOH, 3-COOH, 4-COOH, 2,4-(COOH)$_2$, 2-OCH$_3$, 3-OCH$_3$, 4-OCH$_3$, 3,4,5-(OCH$_3$)$_3$, 2-NH—CO—CH$_2$Cl, 4-NH—CO—CH$_2$Cl, 2-NH—CO—CH$_2$Br, or 4-NH—CO—CH$_2$Br.

Also disclosed is a physiological tolerable salt of the compound of the formula (I).

The present invention also relates to a pharmaceutical composition comprising an effective amount of at least one compound of the formula (I) and/or a physiologically tolerable salt of the compound of the formula (I), in addition to pharmaceutically suitable excipients, additives, and/or active compounds and auxiliaries.

Examples of suitable forms of the pharmaceutical composition are tablets, coated tablets, injectable solutions, suspensions, emulsions, powders, granules, (micro) capsules, suppositories, and syrups.

Also disclosed in the present invention is a method comprising treating rheumatoid arthritis by administering to a patient an effective amount of the pharmaceutical composition described above.

Also disclosed is a method of treating rheumatoid arthritis comprising administering to a patient the pharmaceutical composition and one of the drugs on the market already used to treat rheumatoid arthritis comprising dexamethasone, ibuprofen, leflunomide, malononitrilamide, diclofenac sodium, diclofenac potassium, naproxen, or naproxen sodium.

SUMMARY, RAMIFICATION, AND SCOPE

In conclusion, the present invention discloses a series of novel analogs of leflunomide for treating rheumatoid arthritis. The results of animal studies indicate these analogs are surprisingly effective for treating rheumatoid arthritis. Also disclosed in the present invention is a method of treating rheumatoid arthritis, which comprises administering to a patient a therapeutically effective amount of a pharmaceutical composition comprising the analog.

Although the description above contains many specificities, these should not be construed as limiting the scope of the invention but as merely providing the illustrations of some of the presently preferred embodiments of this invention. Thus the scope of this invention should be determined by the appended claims and their legal equivalents, rather than by the examples given.

What is claimed is:

1. A compound of the formula (I)

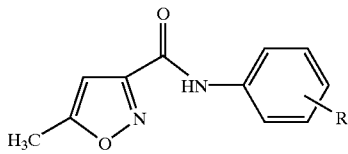

(I)

or a physiological tolerable salt of the compound of the formula (I), wherein R is —H, 2-Cl, 3-Cl, 4-Cl, 2,4-(Cl)$_2$, 2-F, 3-F, 4-F, 2,4-(F)$_2$, 2-Br, 3-Br, 4-Br, 2,4-(Br)$_2$, 3-CF$_3$, 4-CF$_3$, 2,4-(CF$_3$)$_2$, 2-COOH, 3-COOH, 4-COOH, 2,4-(COOH)$_2$, 3-OCH$_3$, 4-OCH$_3$, 3,4,5-(OCH$_3$)$_3$, 2-NH—CO—CH$_2$Cl, 4-NH—CO—CH$_2$Cl, 2-NH—CO—CH$_2$Br, or 4-NH—CO—CH$_2$Br.

2. A pharmaceutical composition comprising a compound of the formula (I)

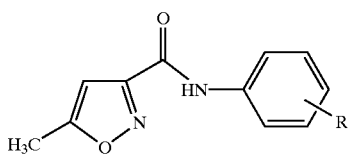

(I)

or a physiological tolerable salt of the compound of the formula (I), wherein R is —H, 2-Cl, 3-Cl, 4-Cl, 2,4-(Cl)$_2$, 2-F, 3-F, 4-F, 2,4-(F)$_2$, 2-Br, 3-Br, 4-Br, 2,4-(Br)$_2$, 3-CF$_3$, 4-CF$_3$, 2,4-(CF$_3$)$_2$, 2-COOH, 3-COOH, 4-COOH, 2,4-(COOH)$_2$, 3-OCH$_3$, 4-OCH$_3$, 3,4,5-(OCH$_3$)$_3$, 2-NH—CO—CH$_2$Cl, 4-NH—CO—CH$_2$Cl, 2-NH—CO—CH$_2$Br, or 4-NH—CO—CH$_2$Br.

3. A method of treating rheumatoid arthritis comprising administering to a patient an effective amount of a pharmaceutical composition comprising a compound of the formula (I)

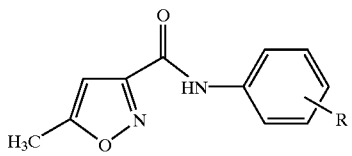

(I)

or a physiological tolerable salt of the compound of the formula (I), wherein R is —H, 2-Cl, 3-Cl, 4-Cl, 2,4-(Cl)$_2$, 2-F, 3-F, 4-F, 2,4-(F)$_2$, 2-Br, 3-Br, 4-Br, 2,4-(Br)$_2$, 2-CF$_3$, 3-CF$_3$, 4-CF$_3$, 2,4-(CF$_3$)$_2$, 2-COOH, 3-COOH, 4-COOH, 2,4-(COOH)$_2$, 2-OCH$_3$, 3-OCH$_3$, 4-OCH$_3$, 3,4,5-(OCH$_3$)$_3$, 2-NH—CO—CH$_2$Cl, 4-NH—CO—CH$_2$Cl, 2-NH—CO—CH$_2$Br, or 4-NH—CO—CH$_2$Br.

4. A method of treating rheumatoid arthritis comprising administering to a patient a therapeutically effective amount of a composition comprising a compound of the formula (I)

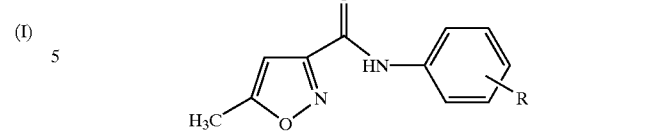

(I)

or a physiological tolerable salt of the compound of the formula (I), wherein R is —H, 2-Cl, 3-Cl, 4-Cl, 2,4-(Cl)$_2$, 2-F, 3-F, 4-F, 2,4-(F)$_2$, 2-Br, 3-Br, 4-Br, 2,4-(Br)$_2$, 2-CF$_3$, 3-CF$_3$, 4-CF$_3$, 2,4-(CF$_3$)$_2$, 2-COOH, 3-COOH, 4-COOH, 2,4-(COOH)$_2$, 2-OCH$_3$, 3-OCH$_3$, 4-OCH$_3$, 3,4,5-(OCH$_3$)$_3$, 2-NH—CO—CH$_2$Cl, 4-NH—CO—CH$_2$Cl, 2-NH—CO—CH$_2$Br, or 4-NH—CO—CH$_2$Br, and a drug selected from the group consisting of dexamethasone, ibuprofen, leflunomide, malononitrilamide, diclofenac sodium, diclofenac potassium, naproxen, naproxen sodium, and combinations thereof.

5. The compound of claim 1 wherein R is H, 2-Cl, 3-Cl, 4-Cl, 3-CF$_3$, 4-CF$_3$, 2,4-(Cl)$_2$, 4-OCH$_3$, 3,4,5-(OCH$_3$)$_3$, 4-COOH, or 4-F.

6. The compound of claim 1 wherein R is H, 2-Cl, 3-Cl, 4-Cl, 4-CF$_3$, 2,4-(Cl)$_2$, 4-COOH, or 4-F.

7. The compound of claim 1 wherein R is 2-Cl, 4-Cl, or 2,4-(Cl)$_2$.

8. The compound of claim 1 wherein R is 2-Cl.

9. The compound of claim 1 wherein R is 4-Cl.

10. The compound of claim 1 wherein R is 2,4-(Cl)$_2$.

11. The pharmaceutical composition of claim 2 wherein R is H, 2-Cl, 3-Cl, 4-Cl, 3-CF$_3$, 4-CF$_3$, 2,4-(Cl)$_2$, 4-OCH$_3$, 3,4,5-(OCH$_3$)$_3$, 4-COOH, or 4-F.

12. The pharmaceutical composition of claim 2 wherein R is H, 2-Cl, 3-Cl, 4-Cl, 4-CF$_3$, 2,4-(Cl)$_2$, 4-COOH, or 4-F.

13. The pharmaceutical composition of claim 2 wherein R is 2-Cl, 4-Cl, or 2,4-(Cl)$_2$.

14. The pharmaceutical composition of claim 2 wherein R is 2-Cl.

15. The pharmaceutical composition of claim 2 wherein R is 4-Cl.

16. The pharmaceutical composition of claim 2 wherein R is 2,4-(Cl)$_2$.

17. The method of claim 3 wherein R is H, 2-Cl, 3-Cl, 4-Cl, 3-CF$_3$, 4-CF$_3$, 2,4-(Cl)$_2$, 4-OCH$_3$, 3,4,5-(OCH$_3$)$_3$, 4-COOH, or 4-F.

18. The method of claim 3 wherein R is H, 2-Cl, 3-Cl, 4-Cl, 4-CF$_3$, 2,4-(Cl)$_2$, 4-COOH, or 4-F.

19. The method of claim 3 wherein R is 2-Cl, 4-Cl, or 2,4-(Cl)$_2$.

20. The method of claim 3 wherein R is 2-Cl.

21. The method of claim 3 wherein R is 4-Cl.

22. The method of claim 3 wherein R is 2,4-(Cl)$_2$.

23. The method of claim 4 wherein R is H, 2-Cl, 3-Cl, 4-Cl, 3-CF$_3$, 4-CF$_3$, 2,4-(Cl)$_2$, 4-OCH$_3$, 3,4,5-(OCH$_3$)$_3$, 4-COOH, or 4-F.

24. The method of claim 4 wherein R is H, 2-Cl, 3-Cl, 4-Cl, 4-CF$_3$, 2,4-(Cl)$_2$, 4-COOH, or 4-F.

25. The method of claim 4 wherein R is 2-Cl, 4-Cl, or 2,4-(Cl)$_2$.

26. The method of claim 4 wherein R is 2-Cl.

27. The method of claim 4 wherein R is 4-Cl.

28. The method of claim 4 wherein R is 2,4-(Cl)$_2$.

* * * * *